US00PP27035P2

(12) United States Plant Patent
Wood

(10) Patent No.: US PP27,035 P2
(45) Date of Patent: Aug. 9, 2016

(54) ***HYDRANGEA* PLANT NAMED 'SMHMTAU'**

(50) Latin Name: *Hydrangea macrophylla*
Varietal Denomination: SMHMTAU

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 5 days.

(21) Appl. No.: 14/121,370

(22) Filed: Aug. 26, 2014

(51) Int. Cl.
*A01H 5/00* (2006.01)

(52) U.S. Cl.
USPC ..... Plt./250

(58) Field of Classification Search
USPC ..... Plt./250
CPC ..... A01H 5/02; A01H 5/00
See application file for complete search history.

(56) References Cited

PUBLICATIONS https://www.greenwoodnursery.com/page.cfm/Blue-Jangles-Hydrangea/215420; 2014; 2 pages.*

* cited by examiner

*Primary Examiner* — Kent L Bell
(74) *Attorney, Agent, or Firm* — C. A. Whealy

(57) ABSTRACT

A new and distinct cultivar of *Hydrangea* plant named 'SMHMTAU', characterized by its compact, upright, outwardly spreading and mounded plant habit; strong and sturdy stems; remontant flowering habit; thick dark green-colored leaves; mophead-type inflorescences that can easily be "blued" with aluminum sulfate treatments; and good garden performance.

2 Drawing Sheets

Botanical designation: *Hydrangea macrophylla.*
Cultivar denomination: 'SMHMTAU'.

BACKGROUND OF THE INVENTION

The present invention relates to a new and distinct *Hydrangea* plant, botanically known as *Hydrangea macrophylla* and hereinafter referred to by the name 'SMHMTAU'.

The new *Hydrangea* plant is a product of a planned breeding program conducted by the Inventor in Grand Haven, Mich. The objective of the breeding program was to develop new reblooming *Hydrangea* plants with strong stems and attractive inflorescences.

The new *Hydrangea* plant originated from a cross-pollination conducted by the Inventor in June, 2008 of *Hydrangea macrophylla* 'Robert', disclosed in U.S. Plant Pat. No. 20,020, as the female, or seed parent and *Hydrangea macrophylla* 'ES1', not patented, as the male, or pollen, parent. The new *Hydrangea* plant was discovered and selected by the Inventor as a single flowering plant from within the progeny of the stated cross-pollination in a controlled environment in Grand Haven, Mich. in July, 2010.

Asexual reproduction of the new *Hydrangea* plant by softwood cuttings in a controlled environment in Grand Haven, Mich. since July, 2010 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHMTAU'. These characteristics in combination distinguish 'SMHMTAU' as a new and distinct *Hydrangea* plant:

1. Compact, upright, outwardly spreading and mounded plant habit.
2. Strong and sturdy stems.
3. Remontant flowering habit.
4. Thick dark green-colored leaves.
5. Mophead-type inflorescences that can easily be "blued" with aluminum sulfate treatments.
6. Good garden performance.

Plants of the new *Hydrangea* differ from plants of the female parent, 'Robert', in the following characteristics:

1. Plants of the new *Hydrangea* are more compact than plants of 'Robert'.
2. Sterile flower sepals of plants of the new *Hydrangea* are richer and more intense in color than sterile flower sepals of plants of 'Robert'.

Plants of the new *Hydrangea* differ from plants of the male parent, 'ES1', in the following characteristics:

1. Plants of the new *Hydrangea* have thicker leaves than plants of 'ES1'.
2. Sterile flower sepals of plants of the new *Hydrangea* are richer and more intense in color than sterile flower sepals of plants of 'ES1'.

Plants of the new *Hydrangea* can be compared to plants of *Hydrangea macrophylla* 'Berner', disclosed in U.S. Plant Pat. No. 22,329. In side-by-side comparisons, plants of the new *Hydrangea* differed primarily from plants of 'Berner' in the following characteristics:

1. Sterile flower sepals of plants of the new *Hydrangea* were richer and more intense in color than sterile flower sepals of plants of 'Berner'.
2. Sterile flower sepals of plants of the new *Hydrangea* had entire margins whereas sterile flower sepals of plants of 'Berner' had serrate margins.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a top perspective view of a typical plant of 'SMHMTAU' grown in an outdoor nursery.

The photograph on the second sheet is a close-up view of a typical inflorescence of 'SMHMTAU'.

DETAILED BOTANICAL DESCRIPTION

Plants used for the aforementioned photographs and the following description were grown during the summer in three-gallon containers and in ground beds in an outdoor nursery in Grand Haven, Mich. and under cultural practices typical of commercial *Hydrangea* production. Plants of the new *Hydrangea* were three years old when the photographs and description were taken. Some plants were treated with aluminum sulfate to "blue" the flowers. In the following description, color references are made to The Royal Horticultural Society Colour Chart, 1995 Edition, except where general terms of ordinary dictionary significance are used.

Botanical description: *Hydrangea macrophylla* 'SMHMTAU'.

Parentage:

*Female, or seed, parent.*—*Hydrangea macrophylla* 'Robert', disclosed in U.S. Plant Pat. No. 20,020.

*Male, or pollen, parent.*—*Hydrangea macrophylla* 'ES1', not patented.

Propagation:

*Type cutting.*—By softwood cuttings.

*Time to initiate roots, summer.*—About 18 days at temperatures about 27° C.

*Time to produce a rooted young plant, summer.*—About 60 days at temperatures about 27° C.

*Root description.*—Fine to thick; white and brown in color.

*Rooting habit.*—Freely branching; dense.

Plant description:

*Plant form and growth habit.*—Perennial deciduous shrub; compact, upright, outwardly spreading and mounded plant habit; inverted triangle; strong and sturdy lateral branches; freely branching habit with about 24 lateral branches developing per plant; vigorous growth habit.

*Plant height.*—About 81 cm.

*Plant diameter or area of spread.*—About 36 cm.

*Lateral branches.*—Length: About 38 cm. Diameter: About 4 mm. Internode length: About 6.5 cm. Texture: Smooth, glabrous. Strength: Strong, sturdy. Aspect: Erect to about 20° from vertical. Color: Close to 145B.

Leaf description:

*Arrangement.*—Opposite, simple.

*Length.*—About 15.5 cm.

*Width.*—About 10.5 cm.

*Shape.*—Elliptic.

*Apex.*—Acuminate.

*Base.*—Obtuse.

*Margin.*—Serrate.

*Texture, upper and lower surfaces.*—Smooth, glabrous; leathery and thick.

*Venation pattern.*—Pinnate.

*Color.*—Developing leaves, upper surface: Close to 143A. Developing leaves, lower surface: Close to 146B. Fully expanded leaves, upper surface: Close to 137A; venation, close to 145C. Fully expanded leaves, lower surface: Close to 146B; venation, close to 145C.

*Petioles.*—Length: About 2 cm. Diameter: About 4 mm. Texture, upper and lower surfaces: Smooth, glabrous. Color, upper and lower surfaces: Close to 145B.

Flower description:

*Flower type and habit.*—Single sterile and fertile flowers arranged on terminal mophead cymes that are roughly hemispherical in shape; flowers face upright to outwardly.

*Fragrance.*—None detected.

*Natural flowering season.*—Plants flower throughout the summer in Grand Haven, Mich.; flowering remontant; flowers persistent.

*Quantity of flowers.*—Freely flowering habit; about 50 fertile flowers and about 210 sterile flowers developing per inflorescence.

*Inflorescence height.*—About 8.5 cm.

*Inflorescence diameter.*—About 14 cm.

*Flower diameter, fertile flowers.*—About 1 cm.

*Flower depth (height), fertile flowers.*—About 5 mm.

*Flower diameter, sterile flowers.*—About 3.3 cm.

*Flower depth (height), sterile flowers.*—About 4 mm.

*Flower buds, fertile and sterile flowers.*—Length: About 5 mm. Diameter: About 3 mm. Shape: Obovate. Color: Close to 1D.

*Petals, fertile flowers only.*—Quantity and arrangement: About five in a single whorl. Length: About 4 mm. Width: About 2 mm. Shape: Ovate. Apex: Acute. Base: Cuneate. Margin: Entire. Texture, upper and lower surfaces: Smooth, glabrous. Color: When opening, upper and lower surfaces: Close to 2D. Fully opened, upper and lower surfaces: Close to 2D.

*Sepals, fertile flowers.*—Quantity and arrangement: If present, four or five in a single whorl. Length: About 1.5 cm. Width: About 2 cm. Shape: Ovate. Apex: Acute. Base: Obtuse. Margin: Entire. Texture, upper and lower surfaces: Smooth, glabrous. Color, not treated with aluminum sulfate: When opening and fully opened, upper surface: Close to between 62A and 68B. When opening and fully opened, lower surface: Close to between 62A and 68B. Color, treated with aluminum sulfate: When opening and fully opened, upper surface: Close to 95D. When opening and fully opened, lower surface: Close to 95D.

*Sepals, sterile flowers.*—Quantity and arrangement: About four to five in a single whorl. Length: About 1.5 cm. Width: About 2 cm. Shape: Ovate. Apex: Acute. Base: Obtuse. Margin: Entire. Texture, upper and lower surfaces: Smooth, glabrous. Color, not treated with aluminum sulfate: When opening and fully opened, upper surface: Close to between 62A and 68B. When opening and fully opened, lower surface: Close to 62A. Color, treated with aluminum sulfate: When opening and fully opened, upper surface: Close to 93C and 100B. When opening and fully opened, lower surface: Close to 94B.

*Pedicels, fertile flowers*.—Angle: About 40° to 50° from inflorescence axis. Strength: Strong, sturdy. Length: About 5 mm. Diameter: About 1 mm. Texture: Pubescent. Color, developing: Close to 4D. Color, developed and not treated with aluminum sulfate: Close to 62A. Color, developed and treated with aluminum sulfate: Close to 96B.

*Pedicels, sterile flowers*.—Angle: About 50° to 60° from inflorescence axis. Strength: Strong, sturdy. Length: About 2.5 cm. Diameter: About 2 mm. Texture: Pubescent. Color, developing: Close to 4D. Color, developed and not treated with aluminum sulfate: Close to 62A. Color, developed and treated with aluminum sulfate: Close to 96B.

*Reproductive organs, observed on fertile flowers only*.—Stamens: Quantity per flower: About ten. Anther shape: Round. Anther length: About 1 mm. Anther color: Close to 4D. Pollen amount: Scarce. Pollen color: Close to 4D. Pistils: Pistil quantity per flower: About three. Pistil length: About 6 mm. Stigma shape: Round. Stigma color: Close to 95A. Style length: About 4 mm. Style color: Close to 99B. Ovary color: Close to 96B.

*Seeds, observed on fertile flowers only*.—Quantity per inflorescence: Numerous. Size: Less than 0.1 mm by less than 0.1 mm; dust-like. Color: Brown.

Disease & pest resistance: Plants of the new *Hydrangea* have not been observed to be resistant to pathogens and pests common to *Hydrangea* plants.

Garden performance: Plants of the new *Hydrangea* have been shown to exhibit good garden performance and to resist sun-scalding. Plants of the new *Hydrangea* have been observed to tolerate temperatures ranging from about −30° C. to about 36° C.

It is claimed:

1. A new and distinct *Hydrangea* plant named 'SMHM-TAU' as illustrated and described.

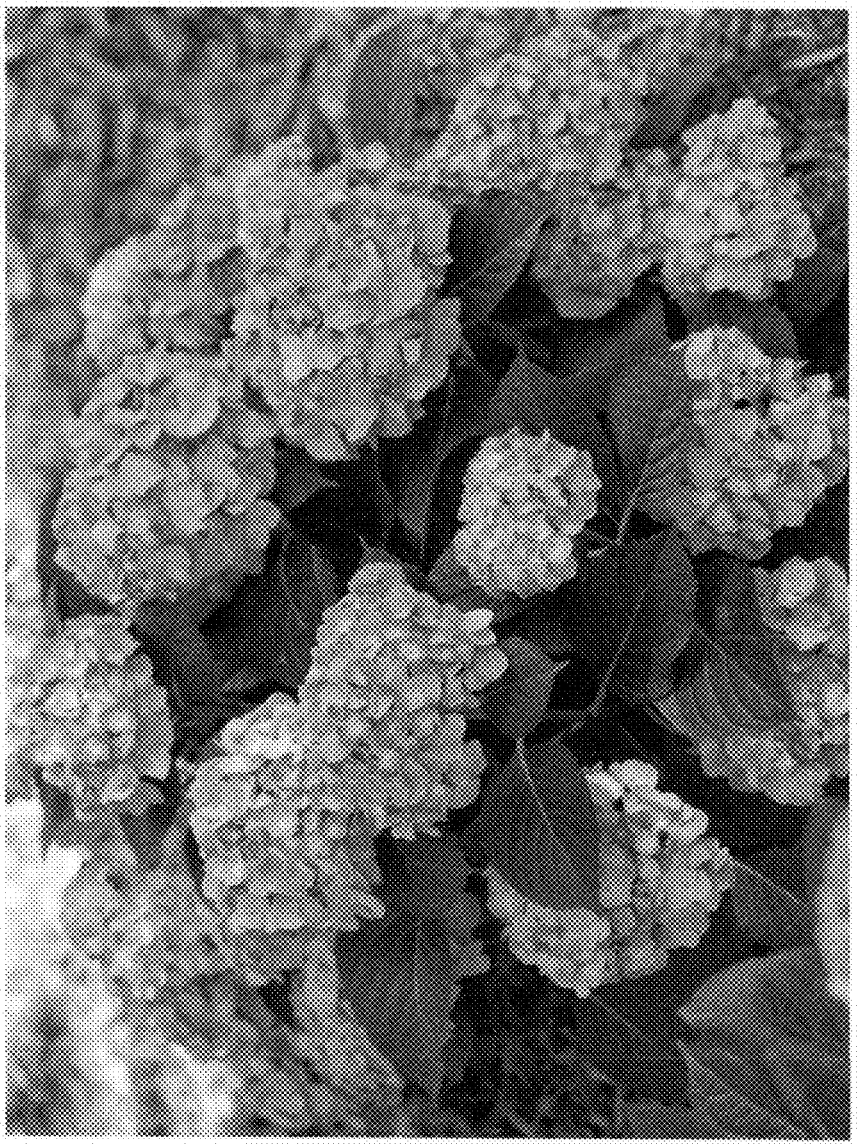

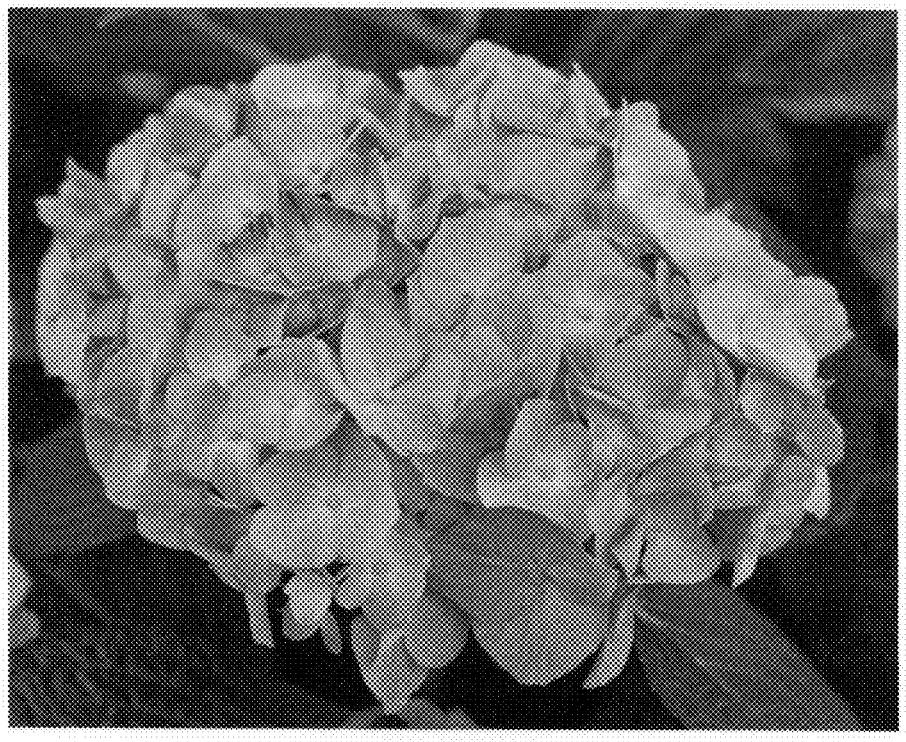

* * * * *